US012692213B2

(12) United States Patent
Jerphagnon et al.

(10) Patent No.: US 12,692,213 B2
(45) Date of Patent: Jul. 28, 2026

(54) REDUCTION BY A SILANE IN THE PRESENCE OF ZINC CATALYST

(71) Applicant: Firmenich SA, Satigny (CH)

(72) Inventors: Thomas Jerphagnon, Satigny (CH); Joel Pastori, Satigny (CH)

(73) Assignee: Firmenich SA (CH)

( * ) Notice: Subject to any disclaimer, the term of this patent is extended or adjusted under 35 U.S.C. 154(b) by 551 days.

(21) Appl. No.: 18/253,914

(22) PCT Filed: Nov. 19, 2021

(86) PCT No.: PCT/EP2021/082257

§ 371 (c)(1),
(2) Date: May 22, 2023

(87) PCT Pub. No.: WO2022/112118

PCT Pub. Date: Jun. 2, 2022

(65) Prior Publication Data

US 2024/0010585 A1 Jan. 11, 2024

(30) Foreign Application Priority Data

Nov. 27, 2020 (EP) .................................... 20020568

(51) Int. Cl.

| | |
|---|---|
| ***C07C 29/147*** | (2006.01) |
| ***B01J 31/18*** | (2006.01) |
| ***B01J 31/22*** | (2006.01) |
| ***C07C 29/14*** | (2006.01) |
| ***C07C 29/143*** | (2006.01) |
| ***C07F 7/18*** | (2006.01) |

(52) U.S. Cl.

CPC ......... *C07C 29/147* (2013.01); *B01J 31/1805* (2013.01); *B01J 31/2239* (2013.01); *B01J 31/2243* (2013.01); *C07C 29/14* (2013.01); *C07C 29/143* (2013.01); *C07F 7/1804* (2013.01); *B01J 2231/64* (2013.01); *B01J 2531/0216* (2013.01); *B01J 2531/26* (2013.01)

(58) Field of Classification Search

CPC ..... C07C 29/147; C07C 29/14; C07C 29/143; C07F 7/1804; B01J 2231/64; B01J 2531/0216; B01J 2531/26

See application file for complete search history.

(56) References Cited

U.S. PATENT DOCUMENTS

| | | | | |
|---|---|---|---|---|
| 6,245,952 B1 | 6/2001 | Mimoun | | |
| 6,573,395 B2 * | 6/2003 | Mimoun | ................ | B01J 31/223<br>568/814 |
| 6,770,588 B2 * | 8/2004 | Mimoun | ................. | C07C 29/14<br>556/124 |

FOREIGN PATENT DOCUMENTS

| | | |
|---|---|---|
| WO | WO 96/12694 | 5/1996 |
| WO | 99/50211 A1 | 7/1999 |

OTHER PUBLICATIONS

Pratt III et al.: "Synthesis and characterization of ionic liquids containing copper, manganese, or zinc coordination cations", Dalton Transactions, vol. 40, No. 43, (Aug. 11, 2011), pp. 11396-11401.
Mimoun et al., Jun. 17, 1999, Enantioselective Reduction of Ketones by Polymethylhydrosiloxane in the Presence of Chiral Zinc Catalysts, J. Am. Chem. Soc., 121(26):6158-6166.
International search report and written opinion dated Jun. 2, 2022, in application No. PCT/EP2021/082257.

* cited by examiner

*Primary Examiner* — Sikarl A Witherspoon
(74) *Attorney, Agent, or Firm* — Knobbe, Martens, Olson & Bear, LLP

(57) ABSTRACT

The present invention relates to the field of organic synthesis. More specifically, it concerns a process for the selective reduction of a $C_3$-$C_{70}$ substrate containing one or more carbonyl or carboxylic functional groups into the corresponding alcohol diol, or polyalcohol in the presence of a silane and at least one catalyst or pre-catalyst in the form of a zinc complex. The Zinc complex of formula (I) or (II) is also part of the invention.

20 Claims, 1 Drawing Sheet

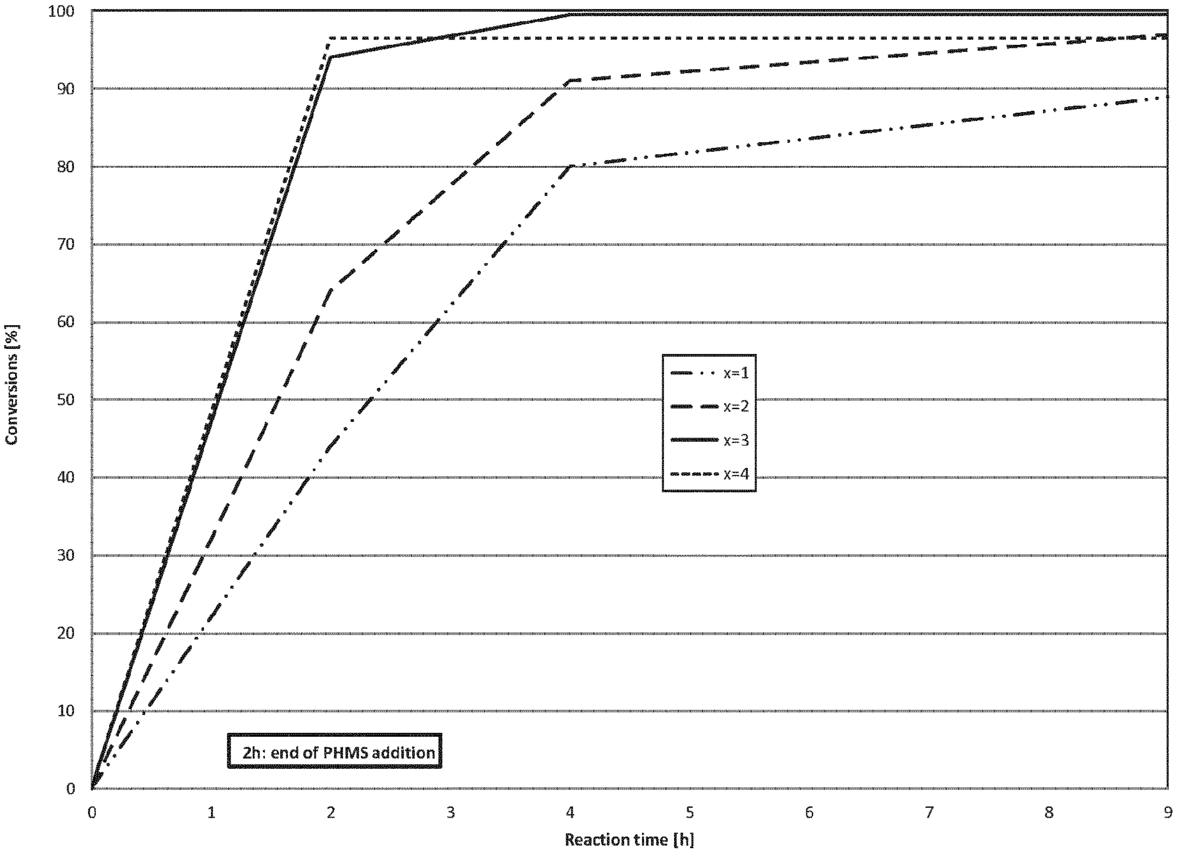
100
90
80
70
60
50
40
30
20
10
0
Conversions [%]
0
1
2
3
4
5
6
7
8
9
Reaction time [h]
x=1
x=2
x=3
x=4
2h: end of PHMS addition

REDUCTION BY A SILANE IN THE PRESENCE OF ZINC CATALYST

This present application is a U.S. national phase entry under 35 U.S.C. § 371 of PCT Application No. PCT/EP2021/082257, filed Nov. 19, 2021, which claims priority to European Patent Application No. 20020568.0, filed Nov. 27, 2020. The entire contents of these applications are explicitly incorporated herein by this reference.

TECHNICAL FIELD

The present invention relates to the field of organic synthesis. More specifically, it concerns a process for the selective reduction of a $C_3$-$C_{70}$ substrate containing one or more carbonyl or carboxylic functional groups into the corresponding alcohol diol, or polyalcohol in the presence of a silane and at least one catalyst or pre-catalyst in the form of a zinc complex. The Zinc complex of formula (I) or (II) is also part of the invention.

BACKGROUND OF THE INVENTION

The selective reduction of a carbonyl functional group such as an aldehyde, a ketone, an carboxylic acid or an ester functional group to the corresponding alcohol is one of the fundamental reactions in organic chemistry, and is used in a large number of chemical processes. In general, two main types of processes are known to achieve such a transformation. Such types of processes are the following:

a) hydride processes, in which a silyl or metal hydride salt, such as $LiAlH_4$, is used;

b) hydrogenation processes, in which molecular hydrogen is used.

Hydride processes are the most versatile one allowing the reduction of the most reactive aldehyde up to the less reactive carboxylic acid but is also the less selective. In addition, metal hydride salts are more difficult to implement in large scale production due to safety issue and represent a costly solution.

So there is a need to develop, without metal hydride salts, a process to reduce selectively all type of carbonyl functional group while limiting even avoiding the reduction of over functional groups such as double bonds.

The present invention provides a solution to the above problem by using silane and at least one catalyst or pre-catalyst in the form of a zinc complex of formula (I) or (II). The selective reduction of carbonyl compounds to the corresponding alcohols using silane and a zinc complex wherein L is 1 or 2 was reported in WO 99/50211. However, the conditions exemplified does not allow reduction of an acid.

SUMMARY OF THE INVENTION

Surprisingly, it has now been discovered that the invention's process allows reducing a large spectrum of substrates while being compatible with the presence of double bond(s).

So, a first object of the present invention is the reduction of a $C_3$-$C_{70}$ substrate containing one or more carbonyl or carboxylic functional groups into the corresponding alcohol, diol, or polyalcohol comprising a) the reaction of the $C_3$-$C_{70}$ substrate containing one or more carbonyl or carboxylic functional groups with a silane and at least one catalyst or pre-catalyst in the form of a zinc complex of formula $ZnX_2L_3$ or (I)

$ZnX_2L'$ (II)

wherein X is an anion and L is an aminoalcohol or thioalcohol, wherein all ligands X are identical or different and all ligands L are identical or different; and L' is of formula (III)

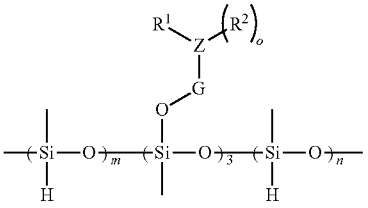

Wherein m represents a integer between 0 and 1000, n represent a integer between 0 and 1000, G represents $C_{1-6}$ hydrocarbon group, optionally comprising one or two oxygen atoms and/or one or two nitrogen atoms, Z represents a nitrogen or a sulphur atom, $R^1$ and $R^2$ are, independently from each other, a hydrogen atom or a $C_{1-3}$ alkyl group, o is 0 when Z is a sulphur atom or o is 1 when Z is a nitrogen atom; and b) the hydrolysis of the obtained siloxane with a basic agent to form an alcohol, a diol or a polyalcohol.

A second object of the invention is a zinc complex of formula $ZnX_2L_3$ or (I)

$ZnX_2L'$ (II)

wherein X is an anion and L is an aminoalcohol or thioalcohol, wherein all ligands X are identical or different and all ligands L are identical or different; and L' is of formula (III)

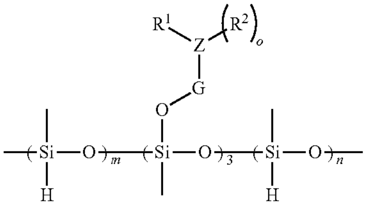

Wherein m represents a integer between 0 and 1000, n represent a integer between 0 and 1000, G represents $C_{1-6}$ hydrocarbon group, optionally comprising one or two oxygen atoms and/or one or two nitrogen atoms, Z represents a nitrogen or a sulphur atom, $R^1$ and $R^2$, are, independently from each other, a hydrogen atom or a $C_{1-3}$ alkyl group and o is 0 when Z is a sulphur atom or o is 1 when Z is a nitrogen atom.

DESCRIPTION OF THE FIGURES

FIG. 1 Conversion in % of 3a,6,6,9a-tetramethyldecahydronaphtho[2,1-b]furan-2(1H)-one into 1-(2-hydroxyethyl)-

2,5,5,8a-tetramethyldecahydronaphthalen-2-ol in function of time using different catalysts.

DESCRIPTION OF THE INVENTION

The invention relates to a novel reduction process using silane and a Zinc catalyst efficient also to reduce less reactive acid or hindered ketone. In meantime, the invention process is very selective and does not reduce other double bond(s) than carbonyl or carboxylic functional groups, such as C═C or C═N, present in the substrates.

So, a first object of the present invention is a process for the reduction of a $C_3$-$C_{70}$ substrate containing one or more carbonyl or carboxylic functional groups into the corresponding alcohol, diol, or polyalcohol comprising a) the reaction of the $C_3$-$C_{70}$ substrate containing one or more carbonyl or carboxylic functional groups with a silane and at least one catalyst or pre-catalyst in the form of a zinc complex of formula $$ZnX_2L_3 \quad \text{or} \tag{I}$$

$$ZnX_2L' \tag{II}$$

wherein X is an anion and L is an aminoalcohol or thioalcohol, wherein all ligands X are identical or different and all ligands L are identical or different; and L' is of formula (III)

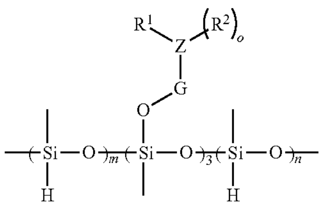

Wherein m represents a integer between 0 and 1000, n represent a integer between 0 and 1000, G represents $C_{1-6}$ hydrocarbon group, optionally comprising one or two oxygen atoms and/or one or two nitrogen atoms, Z represents a nitrogen or a sulphur atom, $R^1$ and $R^2$ are, independently from each other, a hydrogen atom or a $C_{1-3}$ alkyl group, o is 0 when Z is a sulphur atom or o is 1 when Z is a nitrogen atom; and b) the hydrolysis of the obtained siloxane with a basic agent to form an alcohol, a diol or a polyalcohol.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that with the terms " . . . a hydrocarbon group, optionally comprising . . . ", it is meant that said hydrocarbon group optionally comprises alcohol, ketone, aldehyde, ether, ester, carboxylic acid, amine, amide, carbamate or nitrile. These groups can either substitute a hydrogen atom of the hydrocarbon group and thus be laterally attached to said hydrocarbon, or substitute a carbon atom (if chemically possible) of the hydrocarbon group and thus be inserted into the hydrocarbon chain. For example, a —$CH_2$—$CH_2$—CHOH—$CH_2$— group represents a $C_4$ hydrocarbon group comprising an alcohol group (substitution of a hydrogen atom) and, similarly, a —$CH_2$—$CH_2$—O—$CH_2$—$CH_2$—O—$CH_2$—$CH_2$— group represents a $C_6$ hydrocarbon group comprising two ether groups (substitution of carbon atoms/insertion into the hydrocarbon chain).

According to any embodiments of the invention, the use of reducing agents selected in the group of boron or aluminium hydrides, lithium or aluminium alkyls and Grignard compounds, is excluded.

According to any embodiments of the invention, the silane may be selected from the group consisting of arylsilane, diarylsilane, trialkylsilane, dialkylsilane or trialkoxysilane. Non-limiting examples of silane may include phenylsilane, diphenyl silane, dimethylsilane, diethylsilane, trimethoxysilane and triethoxysilane. Particularly, the silane may be polymethylhydrosiloxane (PMHS), phenylsilane or diphenyl silane. Even more particularly, the silane may be polymethylhydrosiloxane (PMHS).

According to any embodiments of the invention, the substrate can be a compound of formula (IV)

(IV)

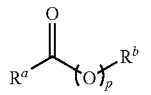

Wherein p is 0 or 1, $R^a$ represents a linear, branched or cyclic $C_1$-$C_{30}$ aromatic, alkyl or alkenyl group, optionally substituted and $R^b$ represents a hydrogen atom, a linear, branched or cyclic $C_1$-$C_{30}$ aromatic, alkyl or alkenyl group, optionally substituted; or $R^a$ and $R^b$ are bonded together and form a $C_4$-$C_{20}$ saturated or unsaturated group, optionally substituted; and wherein the substituents of $R^a$ and $R^b$ are one, two or three halogens, $OR^c$, $NR^c_2$ or $R^c$ groups, in which $R^e$ is a hydrogen atom, a halogenated $C_1$-$C_2$ group or a $C_1$ to $C_{10}$ cyclic, linear or branched alkyl, or alkenyl group.

When p is 1, the corresponding alcohols (i.e (V-a) and (V-b)), or the corresponding diol (V'), obtained by the reduction of substrate (IV), are of formula (V-a)

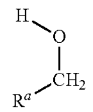

(V-b)

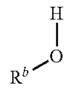

(V')

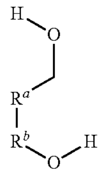

wherein $R^a$ and $R^b$ are defined as in formula (IV).

A compound of formula (V) (i.e. V-a or V-b) will be obtained in the case where $R^a$ and $R^b$ are not bonded together, while a compound of formula (V') will be obtained in the case where $R^a$ and $R^b$ are bonded together.

When p is 0, the corresponding alcohols obtained by the reduction of substrate (IV) are of formula (V-c)

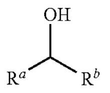

wherein $R^a$ and $R^b$ are defined as in formula (IV).

It is understood that by "a linear, branched or cyclic $C_1$-$C_{30}$ aromatic, alkyl, or alkenyl group" it is meant that said $R^a$ or $R^b$ can be in the form of, e.g., a linear alkyl group or can also be in the form of a mixture of said type of groups, e.g. a specific $R^a$ may comprises a linear alkyl, a branched alkenyl, a (poly)cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyl) it is meant also a group which may comprise moieties having any one of said topologies or unsaturations, as above explained.

According to a further embodiment of the invention, the substrate is a ketone, an aldehyde, a carboxylic acid, an ester, or a lactone that will provide an alcohol or a diol, which is useful in the pharmaceutical, agrochemical or perfumery industry as final product or as an intermediate. Particularly preferred substrate is a ketone, an aldehyde, a carboxylic acid, an ester, or a lactone that will provide an alcohol or diol, which is useful in the perfumery industry as final product or as an intermediate. Even a more particularly preferred substrate is a carboxylic acid, an ester, or a lactone that will provide an alcohol or diol, which is useful in the perfumery industry as final product or as an intermediate.

A particular embodiment of the invention's process is shown in Scheme 1:

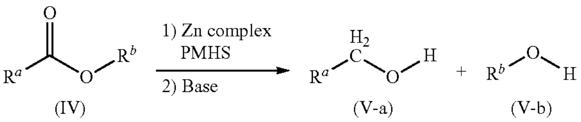

(IV) (V-a) (V-b)

According to any one of the above embodiments of the invention, p is 0 or 1. Preferably p is 1.

According to any one of the above embodiments of the invention, the substrate is a $C_5$-$C_{30}$ compound of formula (IV), and in particular one may cite those wherein $R^a$ and $R^b$ represent simultaneously or independently a linear $C_1$-$C_{30}$ alkyl group optionally substituted, a branched or cyclic $C_3$-$C_{30}$ alkyl or alkenyl group optionally substituted or a $C_5$-$C_{30}$ aromatic group optionally substituted; or $R^a$ and $R^b$ are bonded together and form a $C_4$-$C_{20}$ saturated or unsaturated linear, branched, mono-, di- or tri-cyclic group, optionally substituted.

According to a further embodiment of the invention the substrate is a $C_5$-$C_{20}$ compound of formula (IV), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Possible substituents of $R^a$ and $R^b$ are one, two or three halogens, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of silane used, as well known by a person skilled in the art.

A non-limiting example of aldehyde and ketone may include a linear or branched, aliphatic or cyclic, saturated or unsaturated ketone or aldehyde selected from the group consisting of butanal, pentanal, hexanal, trans-hex-2-en-1-al, heptanal, octanal, decanal, dodecanal, acroleine, methacroleine, crotonaldehyde, prenal, citral, retinal, campholenic aldehyde, cinnamic aldehyde, hexylcinnamic aldehyde, formylpinane, nopal, benzaldehyde, cuminic aldehyde, vanillin, salicylic aldehyde, hexan-2-one, octan-2-one, nonan-4-one, dodecan-2-one, methyl vinyl ketone, mesityl oxide, acetophenone, cyclopentanone, cyclohexanone, cyclododecanone, cyclohex-1-en-3-one, isophorone, oxophorone, carvone, camphor, beta-ionone, geranylacetone, 3-methyl-cyclopenta-1,5-dione, 3,3-dimethyl-5-(2,2,3-trimethyl-cyclopent-3-en-1-yl)-pent-4-en-2-one and 2-pentylcyclopenten-2-one.

A non-limiting example of ester or lactone may include alkyl and aryl acetates, propionates, butyrates, isobutyrates, benzoates, acrylates, crotonates, cinnamates, cis-3-hexenoates, sorbates, salicylates, 10-undecylenates, oleates and linoleates, fatty esters of natural or synthetic origin, caprolactone, butyrolactone, dodecalactone, diketene, sclareolide, spirolactones, allylic ester, di alkyl diesters, (un)substituted benzoic esters, and unsaturated esters such as b-g unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

A non-limiting example of carboxyl acid may include 4-methyl-6-(2,6,6-trimethylcyclohex-1-en-1-yl)hex-3-enoic acid, benzoic acid, butanoic acid, pentanoic acid, $C_{1-30}$ alkyl acid, aryl acid.

According to a further embodiment of the invention the substrate is an animal or vegetable fat. The substrate is a triglyceride of a fatty acid of formula (V)

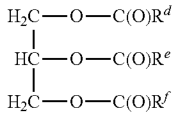

in which $R^d$, $R^e$ and $R^f$ are hydrocarbon groups which are identical or different, linear or branched, saturated or unsaturated, and which can contain from 1 to 20 carbon atoms. Said triglyceride may be a vegetable oil. Non-limiting example of vegetable oil may include oils selected from the group consisting of trioleine, peanut oil, sunflower oil, soya oil, olive oil, colza oil, sesame oil, grapeseed oil, linseed oil, cacao butter, cotton oil, copra oil, coconut oil, palm oil, jojoba oil and palm kernel oil. Non-limiting example of animal fat may be selected from the group consisting of whale sperm, porc, beef, mutton and chicken fat.

According to any embodiments of the invention, X may be an anion selected from the group consisting of carboxylate, b-diketonate, enolate, amide, silylamide, alkyl, cycloalkyl, alkoxy, aryl, aryloxy, alkoxyalkyl, alkoxyaryl, aralkoxy, aralcoyl and alkylaryl groups having from 1 to 20 carbon atoms, halide, carbonate and cyanide. Particularly, X may be selected from the group consisting of acetate, propionate, butyrate, isobutyrate, valerate, isovalerate, diethylacetate (i.e. 2-ethylbutanoate), benzoate, 2-ethylhexanoate, naphthenate, stearate, methoxide, ethoxide, isopropoxide, tert-butoxide, tert-pentoxide, 8-hydroxyquinolinate, substituted and unsubstituted acetylacetonate, tropolonate, a methyl group, an ethyl group, a propyl group, a butyl group and an aryl group.

According to a particular embodiment of the invention, X may be a carboxylate group having from 1 to 20 carbon atoms. In particular, X may be a $R^gCOO$— group wherein $R^g$ may represent a C1-18 alkyl or a phenyl group. Suitable X may be selected from the group consisting of acetate, propionate, butyrate, isobutyrate, valerate, isovalerate, diethylacetate (i.e. 2-ethylbutanoate), benzoate, 2-ethylhexanoate, naphthenate and stearate. Even more particularly, X may be diethylacetate.

According to any embodiments of the invention, L may be an aminoalcohol comprising one or more primary, secondary or tertiary amines functions and one or more primary, secondary or tertiary alcohol functions or L may be a thioalcohol comprising one or more thiol functions and one or more primary, secondary or tertiary alcohol functions. Particularly, L may be an aminoalcohol comprising one or two primary, secondary or tertiary amines functions and one, two or three primary or secondary alcohol functions or L may be a thioalcohol comprising one thiol function and one primary alcohol function. Non-limiting examples suitable aminoalcohol or thioalcohol may be selected from the group consisting of ethanolamine, diethanolamine, triethanolamine, dimethylaminoethanol, diethylaminoethanol, dimethylaminomethanol, diethylaminomethanol, 2-aminobutanol, ephedrine, prolinol, valinol, 2-(Diisopropylamino)ethanol, 2-{[2-(Dimethylamino)ethyl]methylamino}ethanol, 1,3-Bis(dimethylamino)-2-propanol, 2-[2-(Dimethylamino)ethoxy]ethanol, 1-Dimethylamino-2-propanol, 2-(methylthio)ethanol, cinchonidine, quinine and quinidine. Particularly, L may be ethanolamine, diethanolamine, dimethylaminoethanol, 2-{[2-(Dimethylamino)ethyl]methylamino}ethanol, 2-[2-(Dimethylamino)ethoxy]ethanol. Particularly, L may be ethanolamine, diethanolamine, dimethylaminoethanol. Even more particularly, L may be dimethylaminoethanol.

According to any embodiments of the invention, G represents $C_{1-6}$ hydrocarbon group, optionally comprising one oxygen atom. Particularly, G may represent a $C_{1-6}$ alkanediyl group or a $(CH_2)_q$—Y—$(CH_2)_{q'}$ group wherein q and q' are, independently from each other, an integer comprised between 1 and 4 and Y is an oxygen atom or a NH or a $NCH_3$ group. Particularly, G may represent a linear $C_{1-6}$ alkanediyl group, a $(CH_2)_2$—O—$(CH_2)_2$ group or $(CH_2)_2$—$N(CH_3)$—$(CH_2)_2$ group. Particularly, G may represent a $C_{1-3}$ alkanediyl group. Even more particularly, G may be a ethanediyl or a propanediyl group.

According to any embodiments of the invention, Z may be a nitrogen atom.

According to any embodiments of the invention, o may be 1.

According to any embodiments of the invention, L' may be of formula (III')

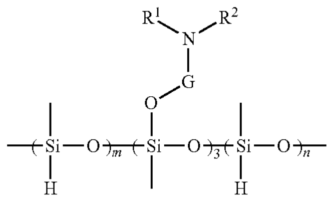

Wherein m, n, G, $R^1$ and $R^2$ have the same meaning as defined above.

According to any embodiments of the invention, $R^1$ and $R^2$ may be, independently from each other, a hydrogen atom or a $C_{1-3}$ alkyl group. Particularly, $R^1$ and $R^2$ may be, independently from each other, a hydrogen atom or a methyl or ethyl group. Even more particularly, $R^1$ and $R^2$ may be a methyl group.

According to any embodiments of the invention, m may be an integer comprised between 0 and 500.

According to any embodiments of the invention, n may be an integer comprised between 0 and 500.

According to any embodiments of the invention, the zinc complex of formula (II) is formed in situ by the reaction between PMHS and zinc complex of formula (I).

In general, the complexes of formulas (I) and (II) can be prepared and isolated prior to their use in the process according to the general methods described in the literature, such as in *J. Am. Chem. Soc.* 1999, 121, 6158-6166. A method is described in the Examples. The complex of formula (I) may be prepared by reacting Zinc Oxide, $ZnCl_2$, $Zn(OH)_2$, $Zn(SO_4)_2$ or $ZnCO_3$ with at least 2 equivalents of a carboxylic acid and at least 3 equivalents of an aminoalcohol or thioalcohol.

Moreover, the complexes can be prepared in situ, by several methods, in the reaction medium, without isolation or purification, just before their use.

According to a particular embodiment of the invention, the zinc complex is of formula (II).

The zinc complex of formula (I) or (II), an essential parameter of the process, can be added to the reaction medium in a large range of concentrations. As non-limiting examples, one can cite as complex concentration values those ranging from 0.1 mol % to 50 mol % or even more, relative to the amount of substrate. Preferably, the complex concentration will be comprised between 0.2 mol % to 30 mol %. Preferably, the complex concentration will be comprised between 0.5 mol % to 20 mol %. Preferably, the complex concentration will be comprised between 1 mol % to 10 mol %. Even more preferably, the complex concentration will be comprised between 1.5 mol % to 5 mol %. It goes without saying that the optimum concentration of complex will depend, as the person skilled in the art knows, on the nature of the latter, on the nature of the substrate and on the temperature during the process, as well as the desired time of reaction.

The silane can be added to the reaction medium in a large range of concentrations. As non-limiting examples, one can cite as silane concentration values those ranging from 1 to 10 equivalents, relative to the amount of substrate. Preferably, the silane will be comprised between 1.1 and 5 equivalents. It goes without saying that the optimum concentration of silane will depend, as the person skilled in the art knows, on the nature of the latter, on the nature of the zinc complex, on the nature of the substrate and on the temperature during the process, as well as the desired time of reaction.

According to any embodiments of the invention, the basic agent used for the hydrolysis is sodium or potassium hydroxide, lime or sodium carbonate.

The basic agent can be added to the reaction medium in a large range of concentrations. As non-limiting examples, one can cite as the basic agent concentration values those ranging from 1 to 10 equivalents, relative to the amount of substrate. Preferably, the basic agent concentration will be comprised between 2 and 7 equivalents. Even more preferably, the basic agent concentration will be comprised between 2 and 4 equivalents. It goes without saying that the optimum concentration of the basic agent will depend, as the person skilled in the art knows, on the nature of the zinc complex, on the nature of the substrate and on the temperature during the process, as well as the desired time of reaction.

The reduction reaction can be carried out in the presence or absence of a solvent. When a solvent is required or used for practical reasons, then any solvent current in reduction reactions can be used for the purposes of the invention. Non-limiting examples include nitrile solvent such as acetonitrile, aromatic solvents such as benzene, toluene, chlorobenzene, diisopropylbenzene, mesitylene or xylene, hydrocarbon solvents such as hexane, heptane, octane, petroleum ether or cyclohexane, ethers such as tetrahydrofuran, methyltetrahydrofuran, MTBE, 1,4-dioxane or diisopropylether, sulfur solvent such as demethysulfoxide, solvent comprising nitrogen atom such as N,N-dimethylformamide, cyclohexylamine, pyridine or mixtures thereof. The choice of the solvent is a function of the nature of the complex and the person skilled in the art is well able to select the solvent most convenient in each case to optimize the reduction reaction.

The temperature at which the reduction can be carried out is comprised between 0° C. and 210° C., more preferably in the range of between 50° C. and 110° C. Of course, a person skilled in the art is also able to select the preferred temperature as a function of the melting and boiling point of the starting and final products as well as the desired time of reaction or conversion.

The invention's process is applicable to various substrates which may contain unsaturated functionalities other than the carbonyl group such as, for example, olefin, acetylene, nitrile or nitro groups which will not be affected by the reduction reaction; i.e. no isomerization or reduction observed with this functional groups.

The catalyst or the pre-catalyst of the present invention is also novel. So a last object of the present invention is zinc complex complex of the general formula (I) or (II) as defined above.

Another object of the invention is a reductive system comprising a) a silane as defined above, preferably PMHS, and b) zinc complex of formula $$ZnX_2L_3 \quad \text{or} \tag{I}$$

$$ZnX_2L' \tag{II}$$

Wherein X, L and L' have the same meaning as defined above.

A further object of the invention is a reaction product produced by the catalyzed reduction of a carbonyl or carboxylic substrate by a silane to a polysilylether before recovery of the alcohol by hydrolysis, consisting of:

a) zinc complex of formula $$ZnX_2L_3 \quad \text{or} \tag{I}$$

$$ZnX_2L' \tag{II}$$

Wherein X, L and L' have the same meaning as defined above; and b) the reaction product of a carbonyl or carboxylic substrate with a silane.

EXAMPLES

The invention will now be described in further detail by way of the following examples, wherein the abbreviations have the usual meaning in the art, the temperatures are indicated in degrees centigrade (° C.). NMR spectra were acquired using a Bruker Avance III 500 operating at 500 MHz ($^1$H) and 125 MHz ($^{13}$C). Spectra were internally referenced relative to tetramethyl silane 0.0 ppm. $^1$H NMR signal shifts are expressed in d ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift d ppm. IR spectra were measured using a Perkin Elmer UATR Spectrum Two IR spectrometer. GC chromatograms were acquired using an Agilent 6580 Chromatograph equipped with an Agilent J&W DB1 column (10 m×0.1 mm×0.1 mm).

Example 1

Preparation of the Invention Catalyst of Formula (II)

To a suspension of 6.1 g of zinc oxide in 71 mL of toluene was added 17.2 g of diethylacetic acid. The reaction mixture was refluxed and the water is removed via azeotropic distillation. When no more water was formed, 41 mL of toluene were removed via distillation, the reaction mixture was cooled down to 60° C. and 20.0 g of N,N-dimethylaminoethanol were slowly added over 1 h00 and the reaction mixture was stirred for 30 min. 15.3 g of PMHS were added in 3 h at 60° C. leading to 78.2 g of catalyst solution (4.5 wt % Zn).

IR ($cm^{-1}$): 3024, 2959, 2931, 2878, 2823, 2767, 1721, 1634, 1606, 1562, 1495, 1463, 1418, 1378, 1321, 1267, 1038, 951, 885, 839, 806, 768, 728, 695, 648, 553.

$^1H$ NMR (500.1 MHz, $CDCl_3$): $d_H$: 0.16 (11H, m; Si—$CH_3$), 0.90 (12H, t, $CH_3$), 1.47 (8H, m, $CH_2$), 1.58 (H, m, $CH_2$), 2.18 (2H, m, CH), 2.19 (13H, m, $CH_3$), 2.42 (5H, s, $CH_3$), 2.52 (5H, m, $CH_2$), 2.61 (1H, t, $CH_2$), 3.77 (1H, t, $CH_2$), 3.83 (5H, m, $CH_2$)

$^{13}C$ NMR (125.7 MHz, $CDCl_3$): −5.7, −4.6, −4.5, −4.2, 1.6, 12.2, 25.6, 45.7, 45.8, 50.5, 57.9, 60.3, 60.4, 60.9, 61.0, 61.6, 184.4

Example 2

Reduction of Acetophenone Using Catalyst of Formula (II)

2.42 g (1.66 mmol, 0.02 eq) of zinc catalyst solution as prepared in Example 1 (4.5 wt % Zn) was added to 10.0 g (83.23 mmol, 1 eq) of acetophenone in 20 mL of toluene. The reaction mixture was heated at 106° C. and 5.95 g (91.55 mmol, 1.1 eq) PMHS was slowly added in 3 hours. The resulting reaction mixture was slowly added to 19 mL of an aqueous solution of potassium hydroxide 45 at 95° C. and stirred for an extra hour. After removal of the basic aqueous layer, the organic layer was washed with water. The solvent was removed under vacuum and the crude was flash distilled leading to 9.97 g phenylethanol in 98 mol % yield.

Example 3

Reduction of 3a,6,6,9a-tetramethyldecahydronaphtho[2,1-b]furan-2(1H)-one Using Catalyst of Formula (II)

1.16 g (0.80 mmol, 0.02 eq) of zinc catalyst solution as prepared in Example 1 (4.5 wt % Zn) was added to 10 g (40.0 mmol, 1 eq) of 3a,6,6,9a-tetramethyldecahydronaphtho[2,1-b]furan-2(1H)-one in 20 mL of toluene. The reaction mixture was heated at 106° C. and 5.45 g (83.9 mmol, 2.1 eq) PMHS was slowly added in 3 hours. The resulting reaction mixture was slowly added to 17 mL of an aqueous solution of potassium hydroxide 45 at 95° C. and stirred for an extra hour. After removal of the basic aqueous layer, the organic layer was washed with water. The solvent was removed under vacuum and the crude was flash distilled leading to 9.75 g 1-(2-hydroxyethyl)-2,5,5,8a-tetramethyldecahydronaphthalen-2-ol in 96 mol % yield.

Example 4

Reduction of Different Substrates Using Catalyst of Formula (II)

a) General Procedure to Reduce Ketone/Aldehyde

Zinc catalyst solution as prepared in Example 1 (4.5 wt % Zn) was added to 1 eq of the ketone or aldehyde as reported in Table 1 in a solvent indicated in Table 1. The reaction mixture was heated at a temperature indicated in Table 1 and 1.1 to 2 eq. of PMHS was slowly added in 3 hours as reported in Table 1. The resulting reaction mixture was slowly added to an aqueous solution of potassium hydroxide 45 at 95° C. and stirred for an extra hour. After removal of the basic aqueous layer, the organic layer was washed with water. The solvent was removed under vacuum and the crude was flash distilled leading to the desired product as reported in Table.

b) General Procedure to Reduce Ester/Lactone/Acid

Zinc catalyst solution as prepared in Example 1 (4.5 wt % Zn) was added to 1 eq of the ester, lactone or acid as reported in Table 1 in a solvent indicated in Table 1. The reaction mixture was heated at a temperature indicated in Table 1 and 2.1 to 5 eq. of PMHS was slowly added in 3 hours as reported in Table 1. The resulting reaction mixture was slowly added to an aqueous solution of potassium hydroxide 45 at 95° C. and stirred for an extra hour. After removal of the basic aqueous layer, the organic layer was washed with water. The solvent was removed under vacuum and the crude was flash distilled leading to the desired product as reported in Table 1.

TABLE 1

Reduction of different substrates using catalyst of formula (II)

| Substrate | Product | % mol [Zn] | Eq. mol. PMHS | Solvant/ Temperature [° C.] | Yield [mol %] |
|---|---|---|---|---|---|
| 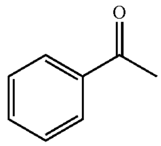 | 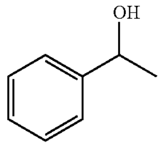 | 2 | 1.1 | Toluene 106° C. | 98 |
| 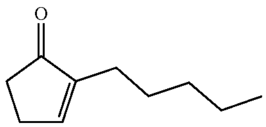 | 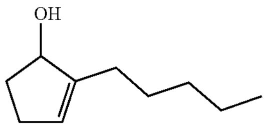 | 2 | 1.3 | Toluene 106° C. | 87 |

TABLE 1-continued
Reduction of different substrates using catalyst of formula (II)
| Substrate | Product | % mol [Zn] | Eq. mol. PMHS | Solvant/ Temperature [° C.] | Yield [mol %] |
|---|---|---|---|---|---|
| 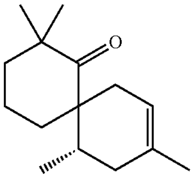 [SMILES: CC1=CCC2(CCCC(C)(C)C2=O)[C@@H](C)C1] | 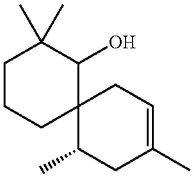 [SMILES: CC1=CCC2(CCCC(C)(C)C2O)[C@@H](C)C1] | 3 | 1.9 | Heptane 96° C. | 83 |
| 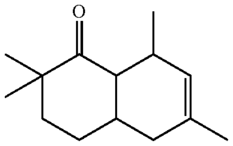 | 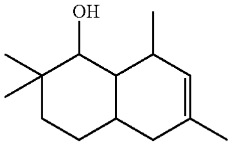 | 3 | 1.9 | Heptane 96° C. | 72 |
| 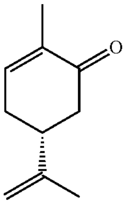 | 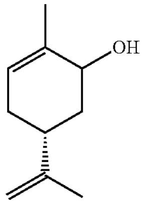 | 2 | 1.2 | Toluene | 92 |
| 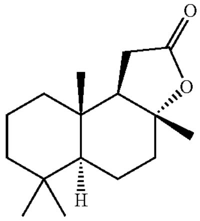 [SMILES: CC1(C)CCC[C@]2(C)[C@H]3CC(=O)O[C@]3(C)CC[C@@H]12] | 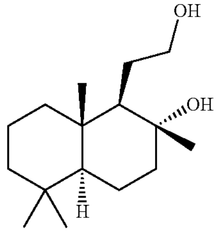 [SMILES: CC1(C)CCC[C@]2(C)[C@@H](CCO)[C@](C)(O)CC[C@@H]12] | 4 | 2.1 | Toluene 106° C. | 96 |
| 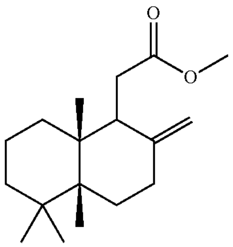 [SMILES: C=C1CC[C@]2(C)C(C)(C)CCC[C@]2(C)C1CC(=O)OC] | 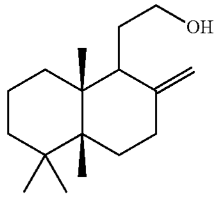 [SMILES: C=C1CC[C@]2(C)C(C)(C)CCC[C@]2(C)C1CCO] | 2 | 2.3 | Toluene 106° C. | 90 |
| 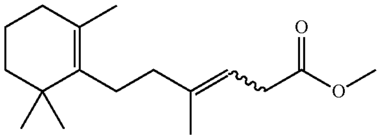 | 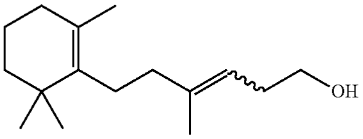 [SMILES: CC(=CCCO)CCC1=C(C)CCCC1(C)C] | 2 | 2 | Heptane 96° C. | 92 |
| 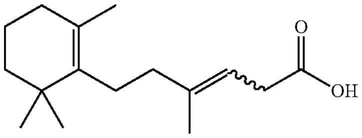 [SMILES: CC(=CCC(=O)O)CCC1=C(C)CCCC1(C)C] | 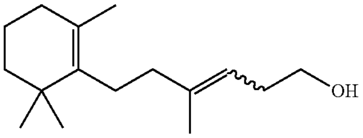 [SMILES: CC(=CCCO)CCC1=C(C)CCCC1(C)C] | 4.5 | 4.8 | Toluene 106° C. | 85 |
| 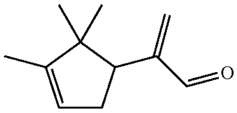 | 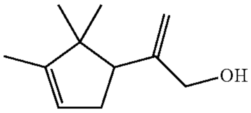 | 2 | 1.1 | Toluene 106° C. | 90 |

TABLE 1-continued

| Reduction of different substrates using catalyst of formula (II) | | | | | |
|---|---|---|---|---|---|
| Substrate | Product | % mol [Zn] | Eq. mol. PMHS | Solvant/ Temperature [° C.] | Yield [mol %] |
| 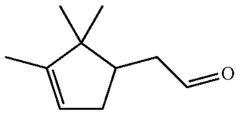 | 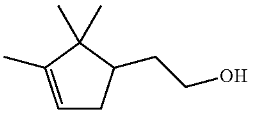 | 2 | 1.1 | Toluene 106° C. | 92 |
| 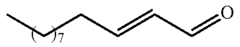 | 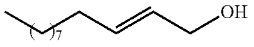 | 2 | 1.1 | Toluene 106° C. | 92 |

As shown in Table 1, the invention's process allows reducing different substrates from aldehyde to acid providing the desired alcohol in high yield while being very selective; i.e. without over reduction or isomerization of carbon-carbon double bond(s) present in the substrate.

Example 5

Comparative Example—Reduction 3a,6,6,9a-tetramethyldecahydronaphtho[2,1-b]furan-2(1H)-one Using Catalyst of Formula (I) or Comparative Catalysts 2.5 mol % of zinc catalyst of formula Zn(diethylacetate)$_2$(dimethylaminoethanol)$_x$ wherein x is 1 (comparative example—catalyst reported in WO 99/50211), 2 (comparative example—catalyst reported in WO 99/50211), 3 (invention's catalyst of formula (I)) or 4 (comparative catalyst) was added to 10 g (40.0 mmol, 1 eq) of 3a,6,6,9a-tetramethyldecahydronaphtho[2,1-b]furan-2(1H)-one in 20 mL of toluene. The reaction mixture was heated at 108° C. and 5.71 g (88 mmol, 2.1 eq) PMHS was slowly added in 2 hours. The conversion was followed by GC and shown in FIG. 1.

As shown in FIG. 1, the highest conversion was obtained with the invention's catalyst. In addition, the invention's catalyst was the most active with the highest conversion after 1 h. Similar activity after 1 h, was observed with comparative catalyst wherein x was 4. However, after 2 h the maximum conversion was obtained with this catalyst without any further increase indicating the deactivation of the catalyst. In other words, the invention's catalyst allows obtaining the best conversion while being very active.

Example 6

Reduction of Acetophenone Using Catalyst of Formula (II) and Various Silane

The reduction has been performed as reported in Example 2 using different silanes (1.1 eq) as indicated in Table 2.

TABLE 2

| Reduction of acetophenone using catalyst of formula (II) and various silane | |
|---|---|
| Silane | Conversion [%] |
| PMHS | 99.3 |
| Phenylsilane | 99.7 |
| Diphenylsilane | 99.5 |

Example 7

Reduction of Acetophenone Using Various Amount of Catalyst of Formula (II)

The reduction has been performed as reported in Example 2 by varying the amount of zinc catalyst as indicated in Table 3.

TABLE 3

| Reduction of acetophenone using various amount of catalyst of formula (II) | |
|---|---|
| mol % Zn | Conversion [%] |
| 0 | 0.0 |
| 0.2 | 89.2 |
| 0.5 | 99.0 |
| 1.0 | 99.4 |
| 2.0 | 99.2 |
| 5.0 | 99.2 |
| 10.0 | 100.0 |

Example 8

Reduction of Acetophenone Using Catalyst of Formula (II) in Various Solvent

The reduction has been performed as reported in Example 2 in different solvents (2 wt eq.) as indicated in Table 4.

TABLE 4

| Reduction of acetophenone using catalyst of formula (II) in various solvents | |
|---|---|
| Solvent | Conversion [%] |
| THF | 99.6 |
| MeTHF | 99.5 |
| iPr$_2$O | 99.5 |
| MeCN | 99.2 |
| Heptane | 99.2 |
| PhMe | 99.1 |
| Chlorobenzene | 99.1 |
| DMSO | 81.9 |
| DMF | 85.5 |
| Cyclohexylamine | 96.1 |
| Pyridine | 98.5 |
| 1,4-Dioxane | 99.1 |

Example 9

Reduction of Acetophenone Using Catalyst of Formula (II) with Various L Ligand

The reduction has been performed as reported in Example 2 using different zinc catalyst of formula (II) with various L ligand as indicated in Table 5 prepared as reported in Example 1.

TABLE 5

Reduction of acetophenone using catalyst of formula (II) with various L ligand

| Ligand | Conversion [%] |
|---|---|
| 2-Dimethylamino Ethanol | 99.1 |
| 2-{[2-(Dimethylamino) Ethyl] Methylamine} Ethanol | 94.2 |
| 2-[2-(Dimethylamino) Ethoxy] Ethanol | 93.4 |

The invention claimed is:

1. Process for the reduction of a $C_3$-$C_{70}$ substrate containing one or more carbonyl or carboxylic functional groups into the corresponding alcohol, diol, or polyalcohol, the process comprising a) reacting the $C_3$-$C_{70}$ substrate containing one or more carbonyl or carboxylic functional groups with a silane and at least one catalyst or pre-catalyst in the form of a zinc complex of formula $ZnX_2L_3$ (I) or $ZnX_2L'$ (II)

wherein X is an anion and L is an aminoalcohol or thioalcohol, wherein all ligands X are identical or different and all ligands L are identical or different; and L' is of formula (III);

(III)

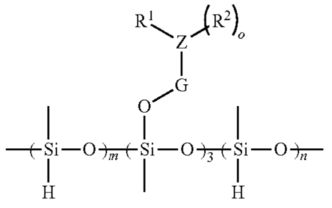

wherein m represents an integer between 0 and 1000, n represent an integer between 0 and 1000, G represents $C_{1-6}$ hydrocarbon group, optionally comprising one or two oxygen atoms and/or one or two nitrogen atoms, Z represents a nitrogen or a sulphur atom, $R^1$ and $R^2$ are, independently from each other, a hydrogen atom or a $C_{1-3}$ alkyl group, o is 0 when Z is a sulphur atom or o is 1 when Z is a nitrogen atom; and b) hydrolyzing the obtained siloxane with a basic agent to form an alcohol, a diol or a polyalcohol.

2. The process according to claim 1, wherein the silane is polymethylhydrosiloxane (PMHS).

3. The process according to claim 2, wherein the zinc complex of formula (II) is formed in situ by the reaction between PMHS and zinc complex of formula (I) prior to adding the substrate.

4. The process according to claim 1, wherein X is an anion selected from the group consisting of carboxylate, β-diketonate, enolate, amide, silylamide, alkyl, cycloalkyl, alkoxy, aryl, aryloxy, alkoxyalkyl, alkoxyaryl, aralkoxy, aralcoyl and alkylaryl groups having from 1 to 20 carbon atoms, halide, carbonate and cyanide.

5. The process according to claim 1, wherein X is selected from the group consisting of acetate, propionate, butyrate, isobutyrate, valerate, isovalerate, diethylacetate, benzoate, 2-ethylhexanoate, naphthenate and stearate.

6. The process according to claim 1, wherein said ligand L is selected from the group consisting of ethanolamine, diethanolamine, triethanolamine, dimethylaminoethanol, diethylaminoethanol, dimethylaminomethanol, diethylaminomethanol, 2-aminobutanol, ephedrine, prolinol, valinol, 2-(Diisopropylamino) ethanol, 2-{[2-(Dimethylamino) ethyl] methylamino} ethanol, 1,3-Bis(dimethylamino)-2-propanol, 2-[2-(Dimethylamino) ethoxy] ethanol, 1-Dimethylamino-2-propanol, cinchonidine, quinine and quinidine.

7. The process according to claim 1, wherein the substrate is a compound of formula (IV):

(IV)

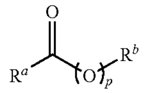

wherein p is 0 or 1, $R^a$ represents a linear, branched or cyclic $C_1$-$C_{30}$ aromatic, alkyl or alkenyl group, optionally substituted and $R^b$ represents a hydrogen atom, a linear, branched or cyclic $C_1$-$C_{30}$ aromatic, alkyl or alkenyl group, optionally substituted; or $R^a$ and $R^b$ are bonded together and form a $C_4$-$C_{20}$ saturated or unsaturated group, optionally substituted; and wherein the substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

8. The process according to claim 1, wherein the substrate is a linear or branched, aliphatic or cyclic, saturated or unsaturated ketone or aldehyde selected from the group consisting of butanal, pentanal, hexanal, trans-hex-2-en-1-al, heptanal, octanal, decanal, dodecanal, acroleine, methacroleine, crotonaldehyde, prenal, citral, retinal, campholenic aldehyde, cinnamic aldehyde, hexylcinnamic aldehyde, formylpinane, nopal, benzaldehyde, cuminic aldehyde, vanillin, salicylic aldehyde, hexan-2-one, octan-2-one, nonan-4-one, dodecan-2-one, methyl vinyl ketone, mesityl oxide, acetophenone, cyclopentanone, cyclohexanone, cyclododecanone, cyclohex-1-en-3-one, isophorone, oxophorone, carvone, camphor, beta-ionone, geranylacetone, 3-methyl-cyclopenta-1,5-dione, 3,3-dimethyl-5-(2,2,3-trimethyl-cyclopent-3-en-1-yl)-pent-4-en-2-one and 2-pentylcyclopenten-2-one.

9. The process according to claim 1, wherein the substrate is an ester or lactone selected from the group consisting of alkyl and aryl acetates, propionates, butyrates, isobutyrates, benzoates, acrylates, crotonates, cinnamates, cis-3-hexenoates, sorbates, salicylates, 10-undecylenates, oleates and linoleates, fatty esters of natural or synthetic origin, caprolactone, butyrolactone, dodecalactone, diketene and sclareolide.

10. The process according to claim 1, wherein said substrate is carboxylic acid selected from the group consisting of 4-methyl-6-(2,6,6-trimethylcyclohex-1-en-1-yl) hex- 3-enoic acid, benzoic acid, butanoic acid, pentanoic acid and $C_1$-30 alkyl acid or aryl acid.

11. Process according to claim 1, wherein the substrate is an animal or vegetable fat.

12. Process according to claim 11, wherein the substrate is a triglyceride of a fatty acid of formula (V):

(V)

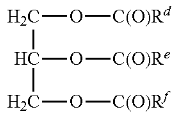

in which $R^d$, $R^e$ and $R^f$ are hydrocarbon groups which are identical or different, linear or branched, saturated or unsaturated, and which can contain from 1 to 20 carbon atoms.

13. Process according to claim 11, wherein said animal or vegetable fat is at least one oil selected from the group consisting of trioleine, peanut oil, sunflower oil, soya oil, olive oil, colza oil, sesame oil, grapeseed oil, linseed oil, cacao butter, cotton oil, copra oil, coconut oil, palm oil, jojoba oil, palm kernel oil, whale sperm oil, and pork, beef, mutton, or chicken fat.

14. The process according to claim 1, wherein the basic agent used for the hydrolysis is sodium or potassium hydroxide, lime or sodium carbonate.

15. A zinc complex of formula $$ZnX_2L_3 \quad \text{or} \qquad \text{(I)}$$

$$ZnX_2L' \qquad \text{(II)}$$

wherein X is an anion and L is an aminoalcohol or thioalcohol, wherein all ligands X are identical or different and all ligands L are identical or different; and L' is of formula (III):

(III)

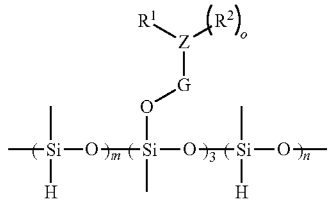

wherein m represents an integer between 0 and 1000, n represent an integer between 0 and 1000, G represents $C_{1-6}$ hydrocarbon group, optionally comprising one or two oxygen atoms and/or one or two nitrogen atoms, Z represents a nitrogen or a sulphur atom, $R^1$ and $R^2$, are, independently from each other, a hydrogen atom or a $C_{1-3}$ alkyl group and o is 0 when Z is a sulphur atom or o is 1 when Z is a nitrogen atom.

16. The process according to claim 3, wherein X is an anion selected from the group consisting of carboxylate, β-diketonate, enolate, amide, silylamide, alkyl, cycloalkyl, alkoxy, aryl, aryloxy, alkoxyalkyl, alkoxyaryl, aralkoxy, aralcoyl and alkylaryl groups having from 1 to 20 carbon atoms, halide, carbonate and cyanide.

17. The process according to claim 3, wherein said ligand L is selected from the group consisting of ethanolamine, diethanolamine, triethanolamine, dimethylaminoethanol, diethylaminoethanol, dimethylaminomethanol, diethylaminomethanol, 2-aminobutanol, ephedrine, valinol, prolinol, 2-(Diisopropylamino) ethanol, 2-{[2-(Dimethylamino) ethyl] methylamino} ethanol, 1,3-Bis(dimethylamino)-2-propanol, 2-[2-(Dimethylamino) ethoxy] ethanol, 1-Dimethylamino-2-propanol, cinchonidine, quinine and quinidine.

18. The process according to claim 3, wherein the substrate is a linear or branched, aliphatic or cyclic, saturated or unsaturated ketone or aldehyde selected from the group consisting of butanal, pentanal, hexanal, trans-hex-2-en-1-al, heptanal, octanal, decanal, dodecanal, acroleine, methacroleine, crotonaldehyde, prenal, citral, retinal, campholenic aldehyde, cinnamic aldehyde, hexylcinnamic aldehyde, formylpinane, nopal, benzaldehyde, cuminic aldehyde, vanillin, salicylic aldehyde, hexan-2-one, octan-2-one, nonan-4-one, dodecan-2-one, methyl vinyl ketone, mesityl oxide, acetophenone, cyclopentanone, cyclohexanone, cyclododecanone, cyclohex-1-en-3-one, isophorone, oxophorone, carvone, camphor, beta-ionone, geranylacetone, 3-methyl-cyclopenta-1,5-dione, 3,3-dimethyl-5-(2,2,3-trimethyl-cyclopent-3-en-1-yl)-pent-4-en-2-one and 2-pentylcyclopenten-2-one.

19. The process according to claim 3, wherein the substrate is an ester or lactone selected from the group consisting of alkyl and aryl acetates, propionates, butyrates, isobutyrates, benzoates, acrylates, crotonates, cinnamates, cis-3-hexenoates, sorbates, salicylates, 10-undecylenates, oleates and linoleates, fatty esters of natural or synthetic origin, caprolactone, butyrolactone, dodecalactone, diketene and sclareolide.

20. The process according to claim 3, wherein the substrate is an animal or vegetable fat, which is at least one oil selected from the group consisting of trioleine, peanut oil, sunflower oil, soya oil, olive oil, colza oil, sesame oil, grapeseed oil, linseed oil, cacao butter, cotton oil, copra oil, coconut oil, palm oil, jojoba oil, palm kernel oil, whale sperm oil, and pork, beef, mutton, or chicken fat.

* * * * *